United States Patent
Mistiniene et al.

(10) Patent No.: US 9,243,049 B2
(45) Date of Patent: Jan. 26, 2016

(54) DERIVATIVES OF RECOMBINANT PROTEINS, HOMO-MULTIMERS OF GRANULOCYTE COLONY-STIMULATING FACTOR AND METHOD OF PREPARATION THEREOF

(75) Inventors: Edita Mistiniene, Vilnius (LT); Jonas Henrikas Pesliakas, Vilnius (LT); Milda Pleckaityte, Vilnius (LT); Gintautas Zvirblis, Vilnius (LT)

(73) Assignee: UAB Profarma, Vilnius (LI)

( * ) Notice: Subject to any disclaimer, the term of this patent is extended or adjusted under 35 U.S.C. 154(b) by 0 days.

(21) Appl. No.: 14/237,807

(22) PCT Filed: Aug. 9, 2011

(86) PCT No.: PCT/LT2011/000009
§ 371 (c)(1),
(2), (4) Date: Feb. 7, 2014

(87) PCT Pub. No.: WO2013/022328
PCT Pub. Date: Feb. 14, 2013

(65) Prior Publication Data
US 2014/0193357 A1 Jul. 10, 2014

(51) Int. Cl.
*C07K 14/52* (2006.01)
*A61K 39/00* (2006.01)
*C07K 14/535* (2006.01)
*C07K 14/56* (2006.01)

(52) U.S. Cl.
CPC .............. *C07K 14/535* (2013.01); *C07K 14/56* (2013.01); *C07K 2319/00* (2013.01); *C07K 2319/31* (2013.01)

(58) Field of Classification Search
None
See application file for complete search history.

(56) References Cited

U.S. PATENT DOCUMENTS

2009/0170163 A1   7/2009   Shen et al.
2010/0189689 A1   7/2010   Chang et al.

FOREIGN PATENT DOCUMENTS

| EP | 1878739 A1 | 1/2008 |  |
| LT | 2010012 A | 8/2011 |  |
| LT | 2010013 A | 8/2011 |  |
| WO | 0103737 A1 | 1/2001 |  |
| WO | 0236626 A1 | 5/2002 |  |
| WO | WO0236626 | * 5/2002 | ........... C07K 14/535 |
| WO | 2009019441 A2 | 2/2009 |  |
| WO | WO2009019441 | * 2/2009 | ............ C07K 14/43 |
| WO | 2010011735 A2 | 1/2010 |  |
| WO | 2011147319 A1 | 12/2011 |  |

OTHER PUBLICATIONS

International Search Report dated Mar. 2, 2012 for PCT/LT2011/000009.
Arai, Ryoichi, et al., "Conformations of Variably Linked Chimeric Proteins Evaluated by Synchrotron X-ray Small-Angle Scattering", Dec. 1, 2004, PROTEINS: Structure, Function, and Genetics, John Wiley & Sons, Inc., US, vol. 57, No. 4, pp. 829-838.
Arai, Ryoichi et al., "Design of the Linkers Which Effectively Separate Domains of a Bifunctional Fusion Protein", Aug. 1, 2001, Protein Engineering, Oxford University Press, vol. 14, No. 8, pp. 529-532.
Cox, George N., et al., "Enhanced Circulating Half-Life and Hematopoietic Properties of a Human Granuloycte Colony-Stimulating Factor/Immunoglobulin Fusion Protein", Jan. 1, 2004, Experimental Hematology, Elsevier Inc., US, vol. 32, pp. 441-449.
Conzelmann, Nadine, et al., "A Screen for Peptide Agonists of the G-CSF Receptor", Jan. 1, 2011, BMC Research Notes, vol. 4, No. 1.

* cited by examiner

*Primary Examiner* — Elly-Gerald Stoica
(74) *Attorney, Agent, or Firm* — Lowenstein Sandler LLP

(57) ABSTRACT

The invention relates to derivatives of recombinant proteins, comprising homo-multimers of genetically fused recombinant biologically active protein monomer units, connected via selected peptide linker moiety; and the method of preparation thereof. Derivative of recombinant protein is preferably dimer of human granulocyte colony-stimulating factor, characterised by increased circulation time in vivo.

12 Claims, 6 Drawing Sheets

```
                         SEQUENCE LISTING

<160> NUMBER OF SEQ ID NOS: 11

<210> SEQ ID NO 1
<211> LENGTH: 11
<212> TYPE: PRT
<213> ORGANISM: Artificial
<220> FEATURE:
<223> OTHER INFORMATION: Linker sequence

<400> SEQUENCE: 1

Ser Gly Gly Gly Gly Ser Gly Gly Gly Gly Ser
1               5                   10

<210> SEQ ID NO 2
<211> LENGTH: 16
<212> TYPE: PRT
<213> ORGANISM: Artificial
<220> FEATURE:
<223> OTHER INFORMATION: Linker sequence

<400> SEQUENCE: 2

Ser Gly Gly Gly Gly Ser Gly Gly Gly Gly Ser Gly Gly Gly Gly Ser
1               5                   10                  15

<210> SEQ ID NO 3
<211> LENGTH: 26
<212> TYPE: PRT
<213> ORGANISM: Artificial
<220> FEATURE:
<223> OTHER INFORMATION: Linker sequence

<400> SEQUENCE: 3

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25

<210> SEQ ID NO 4
<211> LENGTH: 36
<212> TYPE: PRT
<213> ORGANISM: Artificial
<220> FEATURE:
<223> OTHER INFORMATION: Linker sequence

<400> SEQUENCE: 4

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser
```

<210> SEQ ID NO 5
<211> LENGTH: 54
<212> TYPE: PRT
<213> ORGANISM: Artificial
<220> FEATURE:
<223> OTHER INFORMATION: Linker sequence

<400> SEQUENCE: 5

Ser Gly Leu Glu Ala Glu Ala Ala Ala Lys Glu Ala Ala Ala Lys Glu
1               5                   10                  15
Ala Ala Ala Lys Glu Ala Ala Lys Ala Leu Glu Ala Glu Ala Ala
            20                  25                  30
Ala Lys Glu Ala Ala Ala Lys Glu Ala Ala Ala Lys Glu Ala Ala Ala
            35                  40                  45
Lys Ala Leu Glu Gly Ser
        50

<210> SEQ ID NO 6
<211> LENGTH: 347
<212> TYPE: PRT
<213> ORGANISM: Artificial
<220> FEATURE:
<223> OTHER INFORMATION: Protein dimer

<400> SEQUENCE: 6

Met Cys Asp Leu Pro Gln Thr His Ser Leu Gly Ser Arg Arg Thr Leu
1               5                   10                  15
Met Leu Leu Ala Gln Met Arg Lys Ile Ser Leu Phe Ser Cys Leu Lys
            20                  25                  30
Asp Arg His Asp Phe Gly Phe Pro Gln Glu Glu Phe Gly Asn Gln Phe
            35                  40                  45
Gln Lys Ala Glu Thr Ile Pro Val Leu His Glu Met Ile Gln Gln Ile
    50                  55                  60
Phe Asn Leu Phe Ser Thr Lys Asp Ser Ser Ala Ala Trp Asp Glu Thr
65              70                  75                  80
Leu Leu Asp Lys Phe Tyr Thr Glu Leu Tyr Gln Gln Leu Asn Asp Leu
                85                  90                  95
Glu Ala Cys Val Ile Gln Gly Val Gly Val Thr Glu Thr Pro Leu Met
            100                 105                 110
Lys Glu Asp Ser Ile Leu Ala Val Arg Lys Tyr Phe Gln Arg Ile Thr
        115                 120                 125
Leu Tyr Leu Lys Glu Lys Lys Tyr Ser Pro Cys Ala Trp Glu Val Val
    130                 135                 140
Arg Ala Glu Ile Met Arg Ser Phe Ser Leu Ser Thr Asn Leu Gln Glu
145             150                 155                 160
Ser Leu Arg Ser Lys Glu Ser Gly Gly Gly Ser Gly Gly Gly Gly
                165                 170                 175
Ser Gly Gly Gly Gly Ser Cys Asp Leu Pro Gln Thr His Ser Leu Gly
            180                 185                 190
Ser Arg Arg Thr Leu Met Leu Leu Ala Gln Met Arg Lys Ile Ser Leu
        195                 200                 205
Phe Ser Cys Leu Lys Asp Arg His Asp Phe Gly Phe Pro Gln Glu Glu
    210                 215                 220
Phe Gly Asn Gln Phe Gln Lys Ala Glu Thr Ile Pro Val Leu His Glu
225             230                 235                 240

```
Met Ile Gln Gln Ile Phe Asn Leu Phe Ser Thr Lys Asp Ser Ser Ala
                245                 250                 255

Ala Trp Asp Glu Thr Leu Leu Asp Lys Phe Tyr Thr Glu Leu Tyr Gln
            260                 265                 270

Gln Leu Asn Asp Leu Glu Ala Cys Val Ile Gln Gly Val Gly Val Thr
        275                 280                 285

Glu Thr Pro Leu Met Lys Glu Asp Ser Ile Leu Ala Val Arg Lys Tyr
    290                 295                 300

Phe Gln Arg Ile Thr Leu Tyr Leu Lys Glu Lys Tyr Ser Pro Cys
305                 310                 315                 320

Ala Trp Glu Val Val Arg Ala Glu Ile Met Arg Ser Phe Ser Leu Ser
            325                 330                 335

Thr Asn Leu Gln Glu Ser Leu Arg Ser Lys Glu
        340                 345

<210> SEQ ID NO 7
<211> LENGTH: 360
<212> TYPE: PRT
<213> ORGANISM: Artificial
<220> FEATURE:
<223> OTHER INFORMATION: Dimer protein

<400> SEQUENCE: 7

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro Ser
                165                 170                 175

Gly Gly Gly Gly Ser Gly Gly Gly Ser Thr Pro Leu Gly Pro Ala
            180                 185                 190

Ser Ser Leu Pro Gln Ser Phe Leu Leu Lys Cys Leu Glu Gln Val Arg
        195                 200                 205

Lys Ile Gln Gly Asp Gly Ala Ala Leu Gln Glu Lys Leu Cys Ala Thr
    210                 215                 220

Tyr Lys Leu Cys His Pro Glu Glu Leu Val Leu Leu Gly His Ser Leu
225                 230                 235                 240

Gly Ile Pro Trp Ala Pro Leu Ser Ser Cys Pro Ser Gln Ala Leu Gln
                245                 250                 255
```

```
Leu Ala Gly Cys Leu Ser Gln Leu His Ser Gly Leu Phe Leu Tyr Gln
                260                 265                 270

Gly Leu Leu Gln Ala Leu Glu Gly Ile Ser Pro Glu Leu Gly Pro Thr
            275                 280                 285

Leu Asp Thr Leu Gln Leu Asp Val Ala Asp Phe Ala Thr Thr Ile Trp
        290                 295                 300

Gln Gln Met Glu Glu Leu Gly Met Ala Pro Ala Leu Gln Pro Thr Gln
305                 310                 315                 320

Gly Ala Met Pro Ala Phe Ala Ser Ala Phe Gln Arg Arg Ala Gly Gly
                325                 330                 335

Val Leu Val Ala Ser His Leu Gln Ser Phe Leu Glu Val Ser Tyr Arg
            340                 345                 350

Val Leu Arg His Leu Ala Gln Pro
            355                 360

<210> SEQ ID NO 8
<211> LENGTH: 365
<212> TYPE: PRT
<213> ORGANISM: Artificial
<220> FEATURE:
<223> OTHER INFORMATION: Dimer protein

<400> SEQUENCE: 8

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro Ser
                165                 170                 175

Gly Gly Gly Gly Ser Gly Gly Gly Ser Gly Gly Gly Gly Ser Gly Thr
            180                 185                 190

Pro Leu Gly Pro Ala Ser Ser Leu Pro Gln Ser Phe Leu Leu Lys Cys
        195                 200                 205

Leu Glu Gln Val Arg Lys Ile Gln Gly Asp Gly Ala Ala Leu Gln Glu
    210                 215                 220

Lys Leu Cys Ala Thr Tyr Lys Leu Cys His Pro Glu Glu Leu Val Leu
225                 230                 235                 240

Leu Gly His Ser Leu Gly Ile Pro Trp Ala Pro Leu Ser Ser Cys Pro
                245                 250                 255
```

```
Ser Gln Ala Leu Gln Leu Ala Gly Cys Leu Ser Gln Leu His Ser Gly
            260                 265                 270

Leu Phe Leu Tyr Gln Gly Leu Leu Gln Ala Leu Glu Gly Ile Ser Pro
        275                 280                 285

Glu Leu Gly Pro Thr Leu Asp Thr Leu Gln Leu Asp Val Ala Asp Phe
    290                 295                 300

Ala Thr Thr Ile Trp Gln Gln Met Glu Glu Leu Gly Met Ala Pro Ala
305                 310                 315                 320

Leu Gln Pro Thr Gln Gly Ala Met Pro Ala Phe Ala Ser Ala Phe Gln
            325                 330                 335

Arg Arg Ala Gly Gly Val Leu Val Ala Ser His Leu Gln Ser Phe Leu
        340                 345                 350

Glu Val Ser Tyr Arg Val Leu Arg His Leu Ala Gln Pro
    355                 360                 365

<210> SEQ ID NO 9
<211> LENGTH: 375
<212> TYPE: PRT
<213> ORGANISM: Artificial
<220> FEATURE:
<223> OTHER INFORMATION: Dimer protein

<400> SEQUENCE: 9

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro Ser
                165                 170                 175

Gly Gly Gly Gly Ser Gly Gly Gly Gly Ser Gly Gly Gly Gly Ser Gly
            180                 185                 190

Gly Gly Gly Ser Gly Gly Gly Gly Ser Thr Pro Leu Gly Pro Ala Ser
        195                 200                 205

Ser Leu Pro Gln Ser Phe Leu Leu Lys Cys Leu Glu Gln Val Arg Lys
    210                 215                 220

Ile Gln Gly Asp Gly Ala Ala Leu Gln Glu Lys Leu Cys Ala Thr Tyr
225                 230                 235                 240

Lys Leu Cys His Pro Glu Glu Leu Val Leu Leu Gly His Ser Leu Gly
                245                 250                 255
```

```
Ile Pro Trp Ala Pro Leu Ser Ser Cys Pro Ser Gln Ala Leu Gln Leu
            260                 265                 270

Ala Gly Cys Leu Ser Gln Leu His Ser Gly Leu Phe Leu Tyr Gln Gly
        275                 280                 285

Leu Leu Gln Ala Leu Glu Gly Ile Ser Pro Glu Leu Gly Pro Thr Leu
    290                 295                 300

Asp Thr Leu Gln Leu Asp Val Ala Asp Phe Ala Thr Thr Ile Trp Gln
305                 310                 315                 320

Gln Met Glu Glu Leu Gly Met Ala Pro Ala Leu Gln Pro Thr Gln Gly
                325                 330                 335

Ala Met Pro Ala Phe Ala Ser Ala Phe Gln Arg Arg Ala Gly Gly Val
            340                 345                 350

Leu Val Ala Ser His Leu Gln Ser Phe Leu Glu Val Ser Tyr Arg Val
        355                 360                 365

Leu Arg His Leu Ala Gln Pro
    370                 375

<210> SEQ ID NO 10
<211> LENGTH: 385
<212> TYPE: PRT
<213> ORGANISM: Artificial
<220> FEATURE:
<223> OTHER INFORMATION: Dimer protein

<400> SEQUENCE: 10

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro Ser
                165                 170                 175

Gly Gly Gly Gly Ser Gly Gly Gly Ser Gly Gly Gly Gly Ser Gly
            180                 185                 190

Gly Gly Gly Ser Gly Gly Gly Gly Ser Gly Gly Gly Gly Ser Gly Gly
        195                 200                 205

Gly Gly Ser Thr Pro Leu Gly Pro Ala Ser Ser Leu Pro Gln Ser Phe
    210                 215                 220

Leu Leu Lys Cys Leu Glu Gln Val Arg Lys Ile Gln Gly Asp Gly Ala
225                 230                 235                 240
```

```
Ala Leu Gln Glu Lys Leu Cys Ala Thr Tyr Lys Leu Cys His Pro Glu
                245                 250                 255

Glu Leu Val Leu Leu Gly His Ser Leu Gly Ile Pro Trp Ala Pro Leu
            260                 265                 270

Ser Ser Cys Pro Ser Gln Ala Leu Gln Leu Ala Gly Cys Leu Ser Gln
        275                 280                 285

Leu His Ser Gly Leu Phe Leu Tyr Gln Gly Leu Leu Gln Ala Leu Glu
    290                 295                 300

Gly Ile Ser Pro Glu Leu Gly Pro Thr Leu Asp Thr Leu Gln Leu Asp
305                 310                 315                 320

Val Ala Asp Phe Ala Thr Thr Ile Trp Gln Gln Met Glu Glu Leu Gly
                325                 330                 335

Met Ala Pro Ala Leu Gln Pro Thr Gln Gly Ala Met Pro Ala Phe Ala
            340                 345                 350

Ser Ala Phe Gln Arg Arg Ala Gly Gly Val Leu Val Ala Ser His Leu
        355                 360                 365

Gln Ser Phe Leu Glu Val Ser Tyr Arg Val Leu Arg His Leu Ala Gln
    370                 375                 380

Pro
385

<210> SEQ ID NO 11
<211> LENGTH: 403
<212> TYPE: PRT
<213> ORGANISM: Artificial
<220> FEATURE:
<223> OTHER INFORMATION: Dimer protein

<400> SEQUENCE: 11

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro Ser
                165                 170                 175

Gly Leu Glu Ala Glu Ala Ala Lys Glu Ala Ala Lys Glu Ala
            180                 185                 190

Ala Ala Lys Glu Ala Ala Ala Lys Ala Leu Glu Ala Glu Ala Ala Ala
        195                 200                 205
```

-continued

```
Lys Glu Ala Ala Ala Lys Glu Ala Ala Ala Lys Glu Ala Ala Ala Lys
    210                 215                 220

Ala Leu Glu Gly Ser Thr Pro Leu Gly Pro Ala Ser Ser Leu Pro Gln
225                 230                 235                 240

Ser Phe Leu Leu Lys Cys Leu Glu Gln Val Arg Lys Ile Gln Gly Asp
                245                 250                 255

Gly Ala Ala Leu Gln Glu Lys Leu Cys Ala Thr Tyr Lys Leu Cys His
                260                 265                 270

Pro Glu Glu Leu Val Leu Leu Gly His Ser Leu Gly Ile Pro Trp Ala
            275                 280                 285

Pro Leu Ser Ser Cys Pro Ser Gln Ala Leu Gln Leu Ala Gly Cys Leu
    290                 295                 300

Ser Gln Leu His Ser Gly Leu Phe Leu Tyr Gln Gly Leu Leu Gln Ala
305                 310                 315                 320

Leu Glu Gly Ile Ser Pro Glu Leu Gly Pro Thr Leu Asp Thr Leu Gln
                325                 330                 335

Leu Asp Val Ala Asp Phe Ala Thr Thr Ile Trp Gln Gln Met Glu Glu
            340                 345                 350

Leu Gly Met Ala Pro Ala Leu Gln Pro Thr Gln Gly Ala Met Pro Ala
        355                 360                 365

Phe Ala Ser Ala Phe Gln Arg Arg Ala Gly Gly Val Leu Val Ala Ser
    370                 375                 380

His Leu Gln Ser Phe Leu Glu Val Ser Tyr Arg Val Leu Arg His Leu
385                 390                 395                 400

Ala Gln Pro
```

US 9,243,049 B2

DERIVATIVES OF RECOMBINANT PROTEINS, HOMO-MULTIMERS OF GRANULOCYTE COLONY-STIMULATING FACTOR AND METHOD OF PREPARATION THEREOF

FIELD OF THE INVENTION

This invention belongs to the field of protein biotechnology; actually, the present invention provides one of the solutions to the problem of increasing in vivo circulation time of recombinant proteins of therapeutic values. More particularly, the present invention relates to the possibility of preparation of genetically fused homo-multimers of interferon α-2a or granulocyte colony-stimulating factor with extended circulation half-life, comprising at least two monomer units of the protein genetically connected via the linkers of defined length, and efficient isolation and purification of biologically active G-CSF dimers produced. The present invention also relates to a synthetic gene coding for dimer form of human G-CSF containing linker of defined length between G-CSF monomer units for the expression in host cells.

BACKGROUND OF THE INVENTION

In this application the term "protein of therapeutic value" means pharmacologically active protein, suitable for use in therapy and produced through genetic engineering, including mammalian antibodies, blood product substitutes, vaccines, hormones, cytokines. Potential therapeutic proteins are different in a number of important aspects from classical new drug entities, which are generally low-molecular-weight biologically active compounds. To be efficacious, protein drugs are used in concentration and circumstances which differ markedly from their native counterparts and this may lead to undesirable effects in vivo. To avoid or minimise toxicity and increase efficacy both the physicochemical and biological properties of proteins are being altered generally by some form of protein modification e.g., covalent conjugation with other macromolecules, antibody binding, mutagenesis and glycosylation.

The term "biologically active protein" means the protein molecule which exhibit the same detectable biological activity as the respective naturally existing protein.

The term "monomer unit" means a single polypeptide chain of naturally occurring biologically active protein.

The term "homo-multimer" means a linear polypeptide chain consisting of more than one identical biologically active polypeptide subunits, which are connected to each other via peptide linker molecule in a such manner that connection of polypeptide subunit through disulfide bonds is excluded.

The term "genetically fused" means that homo-multimer protein is obtained using recombinant DNA methodology: construction of artificial DNA fragment consisting of two or more connected genes (coding sequences) of monomer proteins via linker DNA sequence, introduction of the DNA fragment into the vector and expression of the protein in the selected cell type. The recombinant protein consists from monomer proteins connected with linker peptide sequences (protein could be isolated after applying special purification procedure) in contrast with "chemically conjugated" protein that is obtained by chemical joining of two or more monomer proteins using specific chemical methods and "chemically modified" protein that is obtained by chemical modification of monomer protein using chemical agents or polymer residues.

Advances in biochemistry, protein chemistry and molecular biology over the last twenty-five years have spurred the increased use and development of recombinant proteins as injectable therapeutic agents. Protein and peptide biopharmaceuticals have been successfully used as very efficient drugs in therapy of many pathophysiological states since the first recombinant product insulin was approved in 1982, One group of approved first generation protein biopharmaceuticals mimics native proteins and serves as replacement therapy, while another group represents monoclonal antibodies for antagonist therapy or activating malfunctioning body proteins [Jevševar S. et al., PEGylation of therapeutic proteins, Biotechnol. J., 5, 113-128 (2010)]. The main drawbacks of the first-generation biopharmaceuticals are their suboptimal physicochemical, pharmacokinetic and pharmacodynamic (PK/PD) properties. Main limitations are physicochemical instability, limited solubility, proteolytic instability, relatively short elimination half-life, immunogenicity and toxicity. Consequently, protein therapeutics are mainly administrated parenterally [Jevševar S. et al., Biotechnol. J., 5, 113-128 (2010)].

Wide range of technologies have been developed during the last decade directed to the development of second-generation biopharmaceuticals encompassing the main products of first-generation protein drugs by conferring to them improved PK/PD characteristics. Extension of in vivo circulating half-life time is the main goal of such therapeutics. Long-acting forms of erythropoietin (EPO, containing two N-linked oligosaccharide chains, under the name of Aranesp), granulocyte colony-stimulating factor (pegylated-G-CSF under the name of Neulasta) and interferons (pegylated IFN alfa-2b under the name of PEG-Intron or pegylated-IFN alfa-2a under the name of Pegasys) are successful examples of second-generation biopharmaceuticals which gained the status of blockbuster drugs.

One of widely used method to prolong plasma half-life time of the target therapeutic protein is chemical modification focusing on increasing the size of therapeutic protein by conjugation with natural or synthetic polymers using well established procedures known as PEGylation (chemical conjugation with polyethylene glycol, Veronese F. M. et al., Protein PEGylation, basic science and biological application in PEGylated Protein Drugs: Basic Science and Clinical Applications, ed. F. M. Veronese, 11-31(2009), polysialylation (chemical conjugation with polysialic acid, Sanjay Jain et al. Polysialylation: The natural way to improve the stability and pharmacokinetics of protein and peptide drugs. dds&s Vol 4 No 1 May (2004), HESylation (chemical conjugation with hydroxyethylstarch, International Patent Application WO 02/080979 and International Patent Application WO 03/000738) and others.

Another method of modification of clearance of therapeutic proteins is through chemical cross-linking or genetic modification to fuse proteins of interest with long-living plasma proteins like albumin, immunoglobulin, or portions of these proteins (Sheffield, Modification of clearance of therapeutic and potentially therapeutic proteins, Curr. Drug Targets Cardiovasc Haematol Disord., 1,1-22, (2001).

Modification of N- and C-terminus of a therapeutic protein or replacement of amino acids which are known to be susceptible for enzymatic cleavage is also used as a strategy to reduce immunogenicity and proteolytic instability and therefore to improve plasma half-life time (Werle M and Bernkop-Schmurrch, Amino acids, 30, 351-367 (2006).

However, all these modifications often cause significant reduction of the biological activity of the protein of interest or elicit antibody formation. Due to this a relatively limited range of proteins with improved plasma half-life time are in clinical use. Therefore, search of new means for alteration of circulation half-life of therapeutic protein remains a challenging task of current biotechnology.

Patent U.S. Pat. No. 5,580,853 describes methods of preparing multimeric erythropoietin derivatives comprising two or more erythropoietin molecules covalently linked together by one or more thioether bond(s). These erythropoietin multimers exhibit increased biological activity and prolonged circulation time. In this method a first erythropoietin derivative was produced by chemically reacting wild type erythropoietin with a hetero-bifunctional cross-linking reagent containing a cleavable disulfide bond group. The disulfide bond was reduced to produce erythropoietin containing a free sulfhydryl group. A second erythropoietin derivative was produced by reacting wild type erythropoietin with a hetero-bifunctional cross-linking reagent containing a maleimido group. The first and second erythropoietin derivatives were reacted together, thereby forming at least one thioether bond between the sulfhydryl and maleimido groups, thus forming a homodimer or homotrimer of erythropoietin. These multimeric erythropoietin molecules exhibit biological activity comparable to wild type erythropoietin and prolonged circulating half-life in vivo, relative to wild type erythropoietin. However, chemical conjugation of protein molecules, e.g., erythropoietin into multimeric form may be accompanied by non-specific chemical modification via functional group of amino acid residue participating in receptor binding. This could decrease the biological activity of the multimeric product. In general, chemical modification may generate unfavourably linked products which must be separated from the correctly linked target product and other by-products. Such modification process is expensive and requires additional purification process steps trying to obtain desired product with reproducible activity and quality characteristics.

EP1334127 discloses single-chain multimeric polypeptides comprising at least two units of a monomeric polypeptide covalently linked via a peptide bond or a peptide linker. Monomeric polypeptide belongs to the protein type that is biologically active in monomeric form. Here, at least one monomeric unit of the construct differs from the corresponding wild-type monomeric polypeptide by at least one added or removed amino acid residue (Lys, Cys, Asp, Glu or His) which serves as an attachment site for further chemical conjugation with non-polypeptide type moiety. The polypeptide is preferably a G-CSF dimer with attached polymer molecule, preferably polyethylene glycol molecules. This patent does not provide any information on the impact of peptide linker on the biological activity of multimeric peptides.

More attractive approach related to production of biologically active multimeric protein derivatives is described in U.S. Pat. No. 5,705,484 that discloses biologically active multimeric polypeptide molecule in which two or more monomeric subunits are linked together as a single polypeptide and prepared as genetically fused multimer. The fusion multimers specifically include PDGF fusion dimers in which protein monomer units are linked via spacer moiety selected from the pre-pro region of a PDGF precursor protein. These fusion multimers are more easily and rapidly refolded than unfused multimers and eliminate the simultaneous formation of undesirable polypeptide by-products during refolding. However, the use of pre-pro sequence as a linker is not favourable due to possible digestion by proteases which commonly participated in the processing of pre-pro domains of a protein molecule.

WO 01/03737 discloses fusion proteins comprising a cytokine or growth factor fused to an immunoglobulin domain, in particular IgG. Also disclosed are multimeric fusion proteins comprising two or more members of the growth hormone superfamily joined with or without a peptide linker. The peptide linker is SerGly, Ser(GlyGlySer)$_n$, wherein n is 1 to 7 or sequences Ser(GlyGlySer) or Ser(GlyGlySer)$_2$. However examples are only provided for fusions with IgG which are regarded as hetero-multimeric fusion proteins.

For separation domains of a bifunctional fusion proteins several lengths of helix-forming peptides linkers with sequence A(EAAAAK)$_n$A (n=2-5) were introduced (R. Arai et all., Prot. Eng., 14 529-532 (2001) showing that such linkers allow controlling the distance and reduce the interference between the domains. This approach is used for separation of different domains of the same type of proteins.

WO2005/034877 describes a polypeptide comprising a G-CSF domain linked to a transferrin domain through Leu-Glu linker. Such fusion can be used for treating various diseases as orally delivered pharmaceutical, but transferrin domain activity is very poor.

Patent U.S. Pat. No. 7,943,733 discloses the role of linker introduced between the partners of hetero-multimers of transferrin-based fusion proteins demonstrating that the insertion of alpha-helical linker between two fusion partners increase the expression level of the fusion. LEA(EAAAK)$_4$ALE sequence between the partner of the fusion comprising a carrier protein (transferrin, serum albumin, antibody and sFV) and therapeutic protein (G-CSF, an interferon, a cytokine, a hormone, a lymphokine, an interleukin, a hematopoietic growth factor and a toxin). However, this patent is dedicated for the production of hetero-fusion construct where protein partners are different protein molecules, representing different activities.

A program to generate all possible linker sequences for fusion proteins has been recently published (C. J. Crasto and J. a. Feng, Prot. Eng., 13, 309-312 (2000). It serves as a tool for rational design of desired linker sequence and its length. However this program could not predict the biologic activity of the final fusion proteins due to complexity of the factors enabling the active structure of the fusion proteins. So, only experimental testing of the different selected linker structures is capable to give the evidence of protein activity.

Thus, among the existing methods for production of long-acting biopharmaceuticals a method of linking monomer unit of the protein of interest into multimers is less time-consuming and allowing to protect multimer construction from the lost of biological activity. However, known method of chemical conjugation of protein monomer into homo-multimers albeit protected biological activity and prolonged circulating half-life did not assure reproducibility of multimer quality parameters.

Method for production of single-chain multimeric polypeptides by introduction into one monomeric unit of amino acid residue for subsequent attachment of PEG in principle mimics well-known methodology of therapeutic protein PEGylation with the only difference that dimer form of the protein instead of monomer is used.

With regards to this, the present invention proposes a method for production of biopharmaceuticals with increased circulation half-life, using genetic fusion of protein monomer units into homo-multimer construct via linkers of defined length. Sequence and structure of the linker is designed to achieve accessibility of each monomer unit to interact with specific receptor of selected monomer of therapeutic protein. Owing to this, no further attachment of polymer, e.g. PEG molecules is required.

Therefore, it is an object of the present invention to provide a multimeric form of therapeutic proteins of interest having biologically active monomer units and improved PK/PD characteristics.

It is a further object of the present invention to provide a multimeric form of therapeutic proteins that can be produced via recombinant DNA technology without formation of undesirable dimer and oligomer forms cross-linked via disulfide bonds.

When molecular mass of the recombinant protein is increased the technologic problems frequently multiply during preparation of the target protein to the purity level in compliance with the requirements for pharmaceutical substance. On the other side the increase of molecular mass of the target protein is associated with the risk of increased propensity for aggregation especially when high expression level of the protein leads to its accumulation in insoluble form (inclusion bodies). In this case technology approaches applied for preparation of monomer protein are no more suitable for isolation and purification of multimeric proteins. Here serious attention should be paid for the proper selection not only of each process stage but also for the compatibility of whole process steps assuring as high as possible biologic activity of the protein with its increased molecular mass at the end of purification cycle. So, this proves the necessity of a new approaches to the preparation of multimeric proteins.

SUMMARY OF THE INVENTION

The present invention provides a new approach for increasing in vivo circulation time of recombinant proteins of therapeutic values, using directed multimerization procedure by genetic fusion of target protein polypeptide chain connected via linker of defined length into dimer, trimer or multimer of desirable length.

Derivatives of recombinant proteins according to present invention comprise homo-multimers of genetically fused recombinant biologically active protein monomer units, connected via suitable peptide linker moiety, wherein protein monomer unit has amino acid sequence of native biologically active protein or essentially the same sequence of at least 95% identity. The suitable linker moiety has an amino acid sequence, selected from the group, consisting of $(S-G_4)_n-S$, wherein n=2-7, and $SGLEA-(EAAAK)_m-ALEA-(EAAAK)_m-ALEGS$, wherein m=2-8, In preferred embodiment of present invention said suitable linker moiety has an amino acid sequence, selected from the group, consisting of SEQ ID No:1, SEQ ID No:2, SEQ ID No:3, SEQ ID No:4 and SEQ ID No:5 below.

In the main aspect of present invention said homo-multimer contains single chain of at least two protein monomer units and said biologically active protein monomer unit is selected from the group, consisting of cytokines, growth factors and hormones, wherein cytokines comprise interleukines, colony stimulating factors or interferons, preferably granulocyte colony stimulating factor (G-CSF) or interferon.

In one preferable embodiment of present invention said biologically active protein monomer unit is recombinant interferon alpha-2a, homo-multimer is dimer, preferably having amino acid sequence SEQ. ID No:6 below.

In another preferred embodiment said biologically active protein monomer unit is recombinant human granulocyte colony-stimulating factor (rhG-CSF).

More specifically homo-multimers of granulocyte colony-stimulating factor according to present invention comprise of least two genetically fused recombinant granulocyte colony-stimulating factor protein monomers, connected via suitable linker moiety defined. Preferred homo-multimer of granulocyte colony-stimulating factor according to present invention is dimer of granulocyte colony-stimulating factor, having amino acid sequence, selected from the group, consisting of SEQ ID No:7, SEQ ID No: 8, SEQ ID No: 9, SEQ ID No:10 and SEQ ID No: 11.

Homo-multimers of granulocyte colony-stimulating factor according to present invention are characterised by increased circulation time in vivo.

Yet another preferred embodiment is homo-multimers of granulocyte colony-stimulating factor for use in therapy. More specifically, homo-multimers of granulocyte colony-stimulating factor according to present invention are intended for the manufacture of the medicament (pharmaceutical substance) for treating of diseases and conditions in indications where monomeric granulocyte colony-stimulating factor protein is used. The related object of present invention is pharmaceutical composition, comprising an therapeutically effective amount of homo-multimer of granulocyte colony-stimulating factor above in combination with pharmaceutically acceptable carrier, diluent, excipient and/or auxiliary substances.

Second main aspect of present invention is a method for preparation of homo-multimers of granulocyte colony-stimulating factor, comprising the steps of:
a) cultivation of microorganism of producer which host cell comprise a nucleotide sequence encoding the target genetically fused protein in a suitable culture medium under conditions, permitting expression of the target proteins;
b) lysing the microorganism of producer and separating the fraction of insoluble target proteins;
c) solubilizing of the fraction of insoluble proteins;
d) renaturation of the target protein;
e) chromatographic purification of the target protein.

The main distinguishing features of the method according to present invention are:
solubilising of the fraction of insoluble proteins is performed in a buffer system, containing urea or guanidine hydrochloride as chaotropic agent;
renaturation is oxidizing renaturation of the target protein from inclusion bodies in the presence of a pair reduced/oxidized glutathione, or metal ions in solution, or immobilized metal ions on chromatography support, and
purification by chromatography consisting of the purification by immobilized metal ions affinity chromatography, and
further additional purification by at least one ion exchange and/or gel-filtration chromatography, or by combination of the ion-exchange chromatography with sequential use of anion-exchange and cation-exchange chromatography.

Finally, dimer of granulocyte colony-stimulating factor according to present invention comprises one, produced by the method according to present invention.

The invention is described below in further details and with reference to the accompanying drawings and examples.

BRIEF DESCRIPTION OF THE DRAWINGS

The preparation of derivatives of recombinant proteins according to present invention and some properties thereof are illustrated by FIGS. 1-7.

Lanes:

M—MW markers from the top: 116; 66,2; 45,0; 35,0; 25; 18,4; 14,4 KDa 1-4—Fractions of desorption of dIFN-2a in ion exchange chromatography on SP-Sepharose FF.

Figure 2:
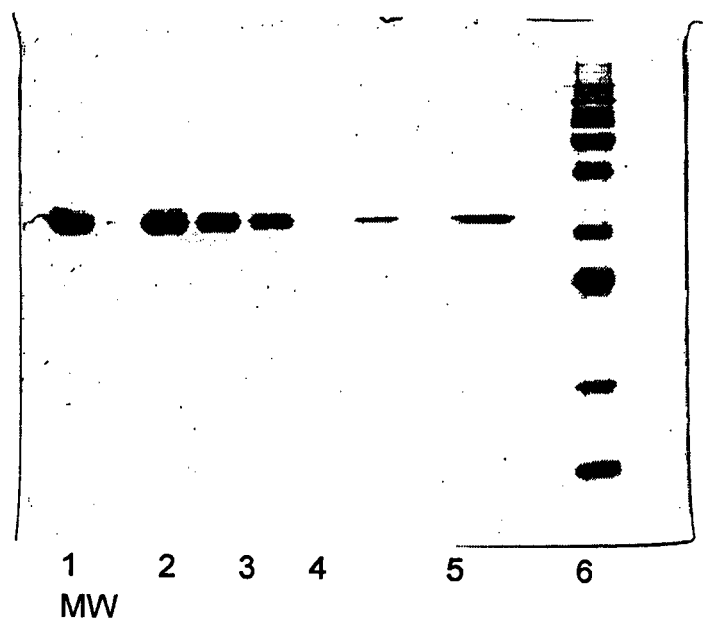

FIG. 2 illustrates SDS-PAGE (15%) of purified dimeric G-CSF-Lα under non-reducing conditions (silver staining).

1-6 lanes—1 μg, 0.5 μg, 0.25 μg, 0.12 μg, 0.06 μg of dimeric G-CSF-Lα respectively.

Figure 3:
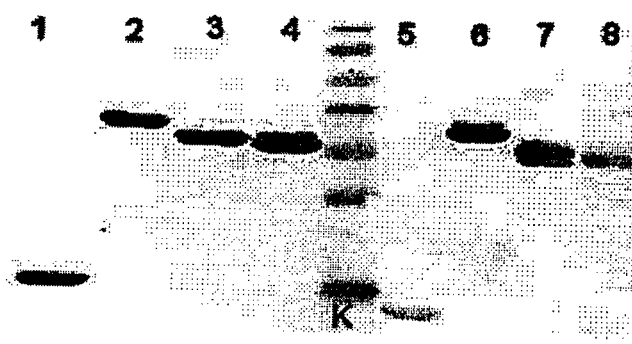

MW—molecular weight standards from the top: 250, 130, 100, 70, 55, 35, 25, 15, 10 kDa FIG. 3 represents Western blot analysis of purified dimeric G-CSF, using monoclonal antibodies against monomeric G-CSF.

Lanes:

1, 5—1 μg monomeric G-CSF in reducing and non-reducing conditions respectively;

2, 6—1 μg dimeric G-CSF with linker Lα in reducing and non-reducing conditions respectively;

3, 7—1 μg dimeric G-CSF with linker L5 in reducing and non-reducing conditions respectively; 4, 8—1 μg dimeric G-CSF with linker L7 in reducing and non-reducing conditions respectively;

K—molecular weight standards from the bottom: 15, 25, 35, 40, 55, 70, 100 kDa.

Figure 4:
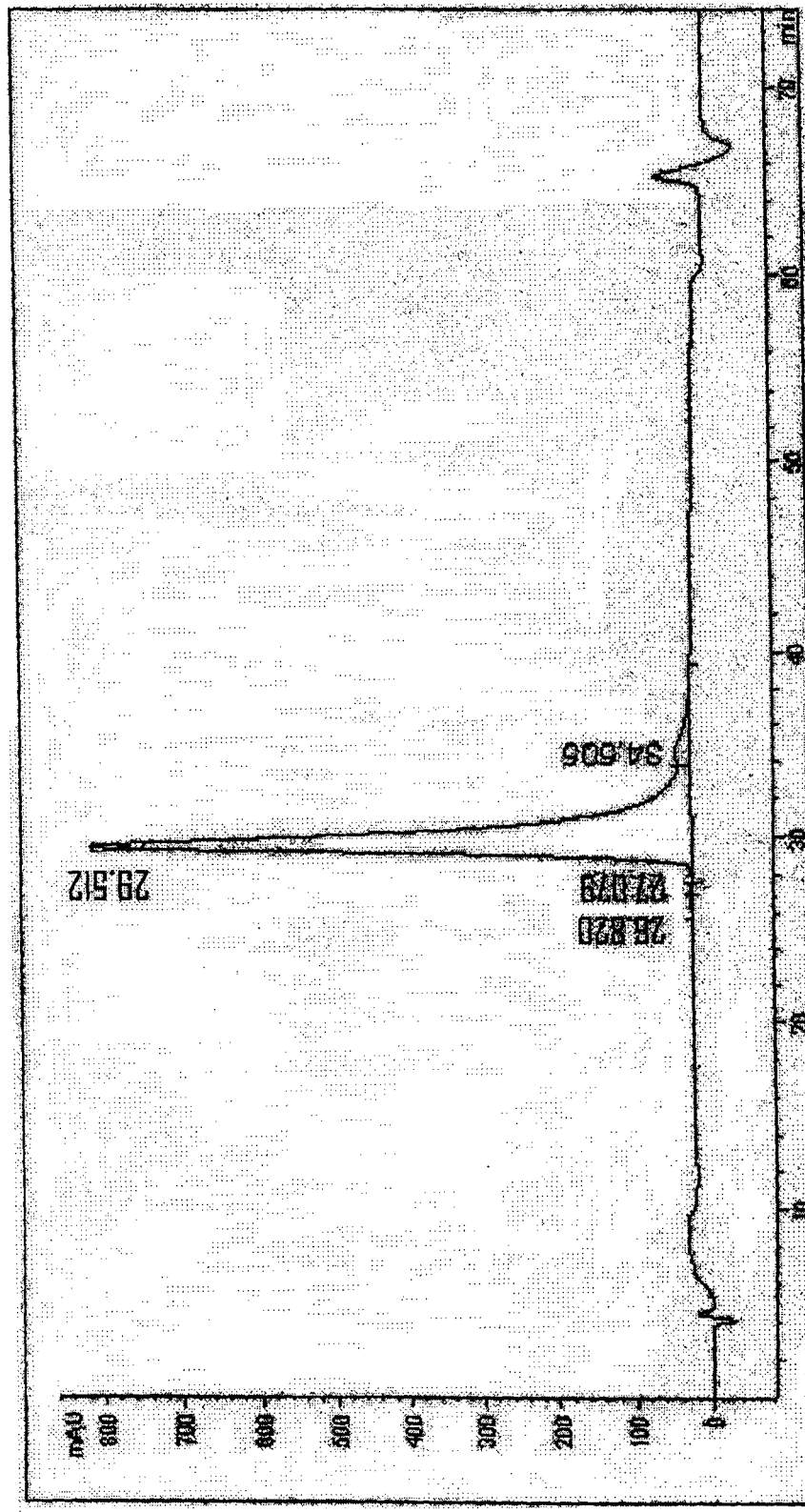

FIG. 4 evidences purity evaluation of dimeric G-CSF-Lα by RP-HPLC, using C4 column ((Hi-Pore RP-304, 250×4.6 mm, 300 Å, "Bio-Rad") and mobile phases: A (0.1% trifluoracetic acid (TFA) aqueous solution) and B (TFA-$H_2O$-acetonitrile 0.1:9.9:90). Loaded amount of protein 50 μg. Detection wave length 215 nm.

Figure 5:
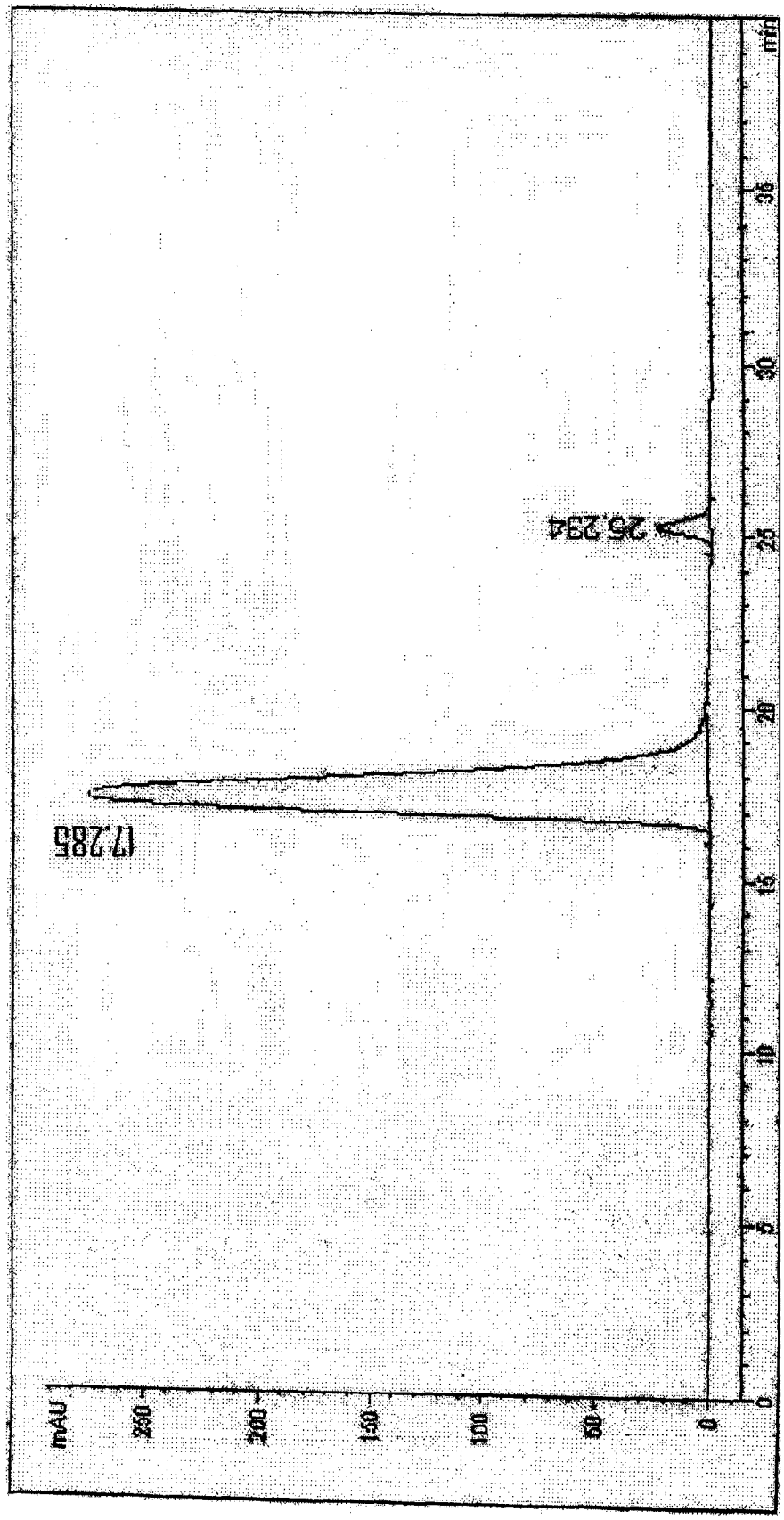

FIG. 5 shows purity evaluation of dimeric G-CSF-Lα by SEC-HPLC, using column TSK-gel G2000 SWXL (7,8×300 mm "Tosoh Bioscience"). Mobile phase 50 mM sodium phosphate buffer, pH 7.2 with 150 mM NaCl. Loaded amount of protein 14 μg. Detection wave length 215 nm.

Figure 6A:
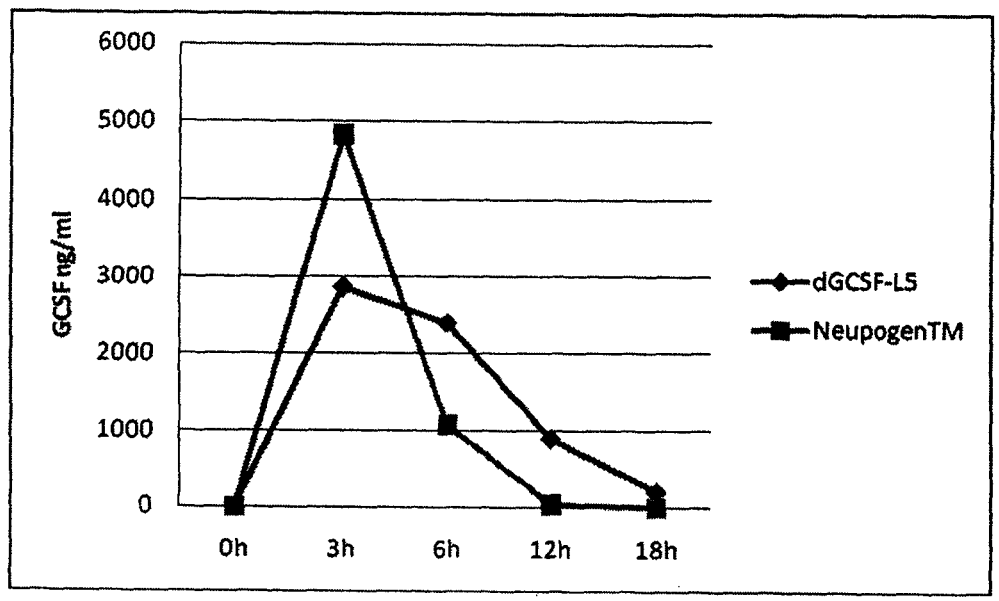
Figure 6B:
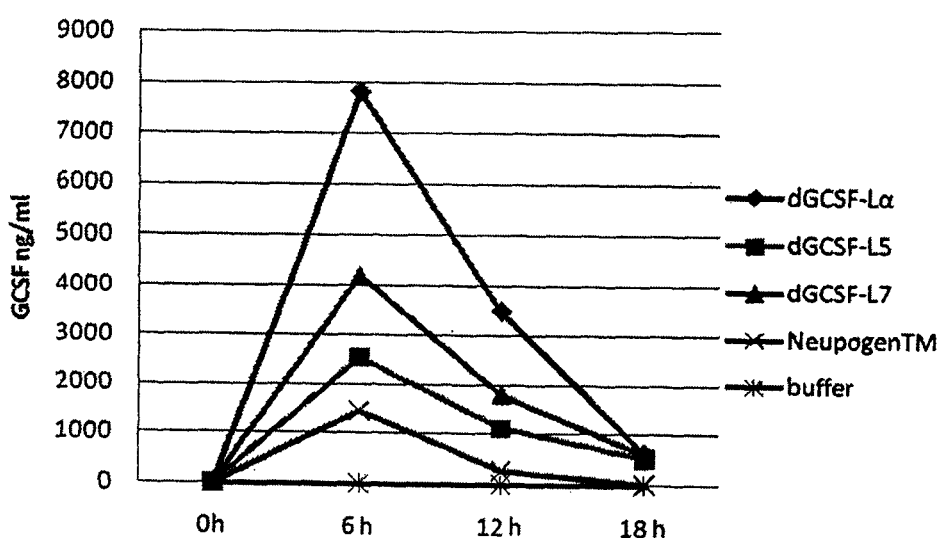

FIG. 6 shows concentration of dimeric G-CSF in rat blood serum after subcutaneous (s.c.) injection (500 μg/kg):

A—dGCSF-L5 and Neupogen™ control;

B—dGCSF-L5, dGCSF-L7, dGCSF-Lα, Neupogen™ control and storage buffer without target protein.

Figure 7:
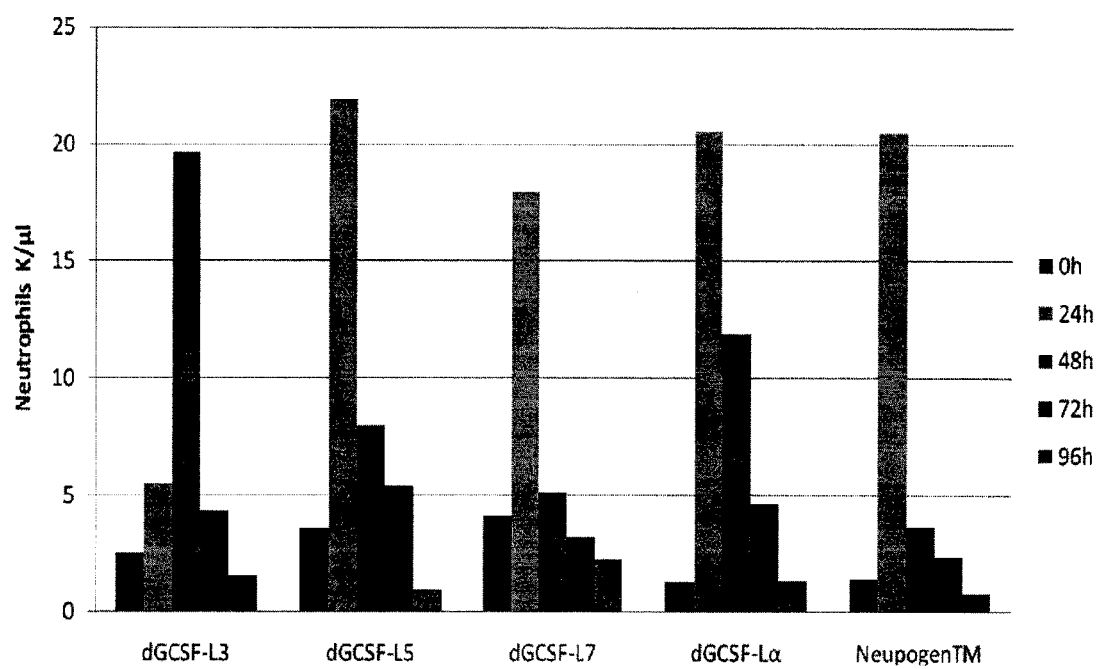

FIG. 7 demonstrates the influence of dimeric G-CSF in vivo on the number of neutrophils in rats after s.c. injection (500 μg/kg). Control probes of Neupogen™ and storage buffer without target protein.

DETAILED DESCRIPTION OF THE INVENTION

Recently (patent U.S. Pat. No. 5,580,853 "'Modified polypeptides with increased biological activity'" inventor— A. J. Sytkowski) it has been reported that chemical cross-linking of erythropoietin protein monomer unit into dimer with hetero-bifunctional cross-linking reagent allow to retain biological activity of obtained dimer comparable to wild type erythropoietin and that the erythropoietin dimer showed a significantly prolonged circulating time in vivo, relative to wild type erythropoietin. Chemical modification frequently generates contaminating products which must be separated from the correctly linked target product. Such modification process is expensive and requires additional purification process steps trying to obtain desired product with reproducible activity and quality characteristics.

The inventors of the present invention have discovered that the genetic fusion of therapeutic protein macromolecule into homo-multimer, particularly homo-dimer connecting monomer units via properly selected sequence and the length of linker molecule, allows to achieve biologically active dimer with enhanced in vivo circulation time. Protein macromolecule to be involved into proposed according to this invention procedure of homo-multimerization encompasses, but is not limited to any therapeutic protein, such as a colony stimulating factor, an interferon, a cytokine, a hormone, an interleukin, a growth factor, antibody fragments and other proteins.

Genetic fusion of therapeutic protein molecule into homo-multimer is achieved with the use of properly selected peptide linker moiety, introduced between monomer units of homo-multimer construction. Linkers suitable for selection are shown in Table 1, Linker molecules of the sequence $(S-G_4)_n$-S, wherein n=2-7 and/or alpha-helical structured sequence of SGLEA-$(EAAAK)_m$-ALEA-$(EAAAK)_m$-ALEGS, wherein m=2-8, are essential linker molecules exemplified in this invention by producing biologically active homo-dimer of granulocyte colony-stimulating factor, which exhibits about two-three time longer circulation time relative to G-CSF monomer, such as Filgrastim (Neupogen™)

TABLE 1

Linkers used for dimeric proteins

| Sequence No: | Label | Linker sequence | Number of amino acids |
|---|---|---|---|
| SEQ ID No: 1 | L2 | $(SG_4)-(SG_4)-S$ | 11 |
| SEQ ID No: 2 | L3 | $(SG_4)-(SG_4)-(SG_4)-S$ | 16 |
| SEQ ID No: 3 | L5 | $(SG_4)-(SG_4)-(SG_4)-(SG_4)-(SG_4)-S$ | 26 |
| SEQ ID No: 4 | L7 | $(SG_4)-(SG_4)-(SG_4)-(SG_4)-(SG_4)-(SG_4)-(SG_4)-S$ | 36 |
| SEQ ID No: 5 | Lα | SGLEA-$(EAAAK)_4$-ALEA-$(EAAAK)_4$-ALEGS | 54 |

The homo-multimers of therapeutic proteins may be expressed in host cells such as bacteria, e.g. *E. coli* BL21 (DE3); yeast; higher eukaryotic cells, e.g. CHO, and others. More preferably, *E. coli* host cells are used for expression of homo-multimers of target therapeutic proteins. Bacteria are excellent producer of different recombinant proteins especially in case of the proteins without additional modifications of the amino acids. Cheap biosynthesis, sufficient yields of recombinant proteins, inability to be infected with mammalian viruses and other infective materials of mammalian origin (if media used is free from additives of mammalian origin) is important advantages of such producers. The strain *E. coli* BL21(DE3) in combination with effective vector pET21b used for illustrating of current invention are able to produce sufficient amounts of target multimeric protein, though recombinant proteins are frequently accumulated as insoluble aggregated and inactive particles. The purification and refolding step of multimeric proteins is critical stage of this invention to obtain biologically active and stable material for further steps.

*E. coli* produced homo-dimers of recombinant human G-CSF are accumulated within the cells as inclusion bodies (IB). With regards to this the procedures for isolation of IB, their purification by established washing procedures and further solubilization in a buffer system containing selected chaotropic agent has been elaborated.

In order to obtain acceptable yield of finally purified target homo-dimer of G-CSF the inclusion body proteins according to preferred embodiment of present invention were reduced during solubilization step in the presence of selected concentration of dithiothreithol (DTT). Proposed according to the present invention process for isolation and purification of homo-dimer of G-CSF comprises solubilization of pre-washed IB in a buffer containing 8 M urea, further dilution of IB solubilizate to defined range of protein concentration and urea concentration of 3 M, oxidative refoding of the protein by one type of established procedure using additives of Cu ions or a pair of reduced SH-agent, such as DTT or glutathione (GSH) and oxidizing agent, such as oxidized glutathione (GSSG) with the use of established concentration of each agent.

More specifically the method according to present invention is characterised in that renaturation of the target protein is performed by any of alternative procedures:

a) in the presence of CuSO4 by mixing at ambient temperature for 1-3 hours, preferably 2 hours, and stopping refolding by adding EDTA solution at pH 5.4±0.2 to final concentration of 5-15 mM, preferably 10 mM; or b) in the presence of a pair reduced(GSH)/oxidized(GSSG) glutathione taken in the concentration ratio 5-10:1 by mixing overnight or preferably for 24-96 hours at the temperature +2-+8° C.; or c) in the presence of 0.08-0.12 mM GSSG by mixing overnight or preferably for 24-96 hours at +2-+8° C.; or d) in the presence of GSSG in such manner that final molar ratio in solution of DTT/GSSG is 1: 1,5-10 by mixing overnight or preferably for 24-96 hours at +2-+8° C.

The refolded target protein is further subjected to chromatography purification step consisting of anion-exchange chromatography of urea-containing refolded protein solution over DEAE-Sepharose FF column. Elution of the target correctly folded homo-dimer of G-CSF has been elaborated with respect to recovery yield. Further, the combined eluate of fractions recovered from DEAE-Sepharose FF column is chromatographied over strong cation-exchanger as SP-Sepharose FF chromatography media. Finally purified homo-dimer of G-CSF is formulated as liquid formulation containing pre-defined concentration of buffer substance, tonicity adjusting agent and non-ionic detergent with its selected type and concentration range sufficient to avoid protein damage at the air/solution interface.

The structure of constructed and expressed dimeric proteins is confirmed using few independent methods such as sequencing of recombinant expression plasmid with subsequent translation of dGCSF gene into protein amino acid sequence and mass-spectrometry analysis of purified proteins (see Table 2).

Table 2

Sequence and molecular mass of dimeric proteins

| Sequence No | Dimeric protein | Molecular mass, kDa | Full amino acid sequence of dimeric protein |
|---|---|---|---|
| SEQ ID No: 6 | dIFN-2a_L3 | 39,63 | MCDLPQTHSLGSRRTLMLLAQMRKISLFSC |
| | | | LKDRHDFGFPQEEFGNQFQKAETIPVLHEM |
| | | | IQQIFNLFSTKDSSAAWDETLLDKFYTELYQ |
| | | | QLNDLEACVIQGVGVTETPLMKEDSILAVRK |
| | | | YFQRITLYLKEKKYSPCAWEWRAEIMRSF |
| | | | SLSTNLQESLRSKESGGGGSGGGGSGGG |
| | | | GSCDLPQTHSLGSRRTLMLLAQMRKISLFS |
| | | | CLKDRHDFGFPQEEFGNQFQKAETIPVLHE |
| | | | MIQQIFNLFSTKDSSAAWDETLLDKFYTELY |
| | | | QQLNDLEACVIQGVGVTETPLMKEDSILAV |
| | | | RKYFQRITLYLKEKKYSPCAWEVVRAEIMR |
| | | | SFSLSTNLQESLRSKE |
| SEQ ID No: 7 | dGCSF-L2 | 38,17 | MTPLGPASSLPQSFLLKCLEQVRKIQGDGA |
| | | | ALQEKLCATYKLCHPEELVLLGHSLGIPWA |
| | | | PLSSCPSQALQLAGCLSQLHSGLFLYQGLL |
| | | | QALEGISPELGPTLDTLQLDVADFATTIWQQ |
| | | | MEELGMAPALQPTQGAMPAFASAFQRRAG |
| | | | GVLVASHLQSFLEVSYRVLRHLAQPSGGG |

-continued

| Sequence No | Dimeric protein | Molecular mass, kDa | Full amino acid sequence of dimeric protein |
|---|---|---|---|
| | | | GSGGGGSTPLGPASSLPQSFLLKCLEQVR |
| | | | KIQGDGAALQEKLCATYKLCHPEELVLLGH |
| | | | SLGIPWAPLSSCPSQALQLAGCLSQLHSGL |
| | | | FLYQGLLQALEGISPELGPTLDTLQLDVADF |
| | | | ATTIWQQMEELGMAPALQPTQGAMPAFAS |
| | | | AFQRRAGGVLVASHLQSFLEVSYRVLRHLA |
| | | | QP |
| SEQ ID No: 8 | dGCSF-L3 | 38,55 | MTPLGPASSLPQSFLLKCLEQVRKIQGDGA |
| | | | ALQEKLCATYKLCHPEELVLLGHSLGIPWA |
| | | | PLSSCPSQALQLAGCLSQLHSGLFLYQGLL |
| | | | QALEGISPELGPTLDTLQLDVADFATTIWQQ |
| | | | MEELGMAPALQPTQGAMPAFASAFQRRAG |
| | | | GVLVASHLQSFLEVSYRVLRHLAQPSGGG |
| | | | GSGGGGSGGGGSTPLGPASSLPQSFLLKC |
| | | | LEQVRKIQGDGAALQEKLCATYKLCHPEEL |
| | | | VLLGHSLGIPWAPLSSCPSQALQLAGCLSQ |
| | | | LHSGLFLYQGLLQALEGISPELGPTLDTLQL |
| | | | DVADFATTIWQQMEELGMAPALQPTQGAM |
| | | | PAFASAFQRRAGGVLVASHLQSFLEVSYRV |
| | | | LRHLAQP |
| SEQ ID N:. 9 | dGCSF-L5 | 39,12 | MTPLGPASSLPQSFLLKCLEQVRKIQGDGA |
| | | | ALQEKLCATYKLCHPEELVLLGHSLGIPWA |
| | | | PLSSCPSQALQLAGCLSQLHSGLFLYQGLL |
| | | | QALEGISPELGPTLDTLQLDVADFATTIWQQ |
| | | | MEELGMAPALQPTQGAMPAFASAFQRRAG |
| | | | GVLVASHLQSFLEVSYRVLRHLAQPSGGG |
| | | | GSGGGGSGGGGSGGGGSGGGGSTPLGP |
| | | | ASSLPQSFLLKCLEQVRKIQGDGAALQEKL |
| | | | CATYKLCHPEELVLLGHSLGIPWAPLSSCP |
| | | | SQALQLAGCLSQLHSGLFLYQGLLQALEGI |
| | | | SPELGPTLDTLQLDVADFATTIWQQMEELG |
| | | | MAPALQPTQGAMPAFASAFQRRAGGVLVA |
| | | | SHLQSFLEVSYRVLRHLAQP |
| SEQ ID No: 10 | dGCSF-L7 | 39,75 | MTPLGPASSLPQSFLLKCLEQVRKIQGDGA |
| | | | ALQEKLCATYKLCHPEELVLLGHSLGIPWA |
| | | | PLSSCPSQALQLAGCLSQLHSGLFLYQGLL |
| | | | QALEGISPELGPTLDTLQLDVADFATTIWQQ |
| | | | MEELGMAPALQPTQGAMPAFASAFQRRAG |

| Sequence No | Dimeric protein | Molecular mass, kDa | Full amino acid sequence of dimeric protein |
|---|---|---|---|
| | | | GVLVASHLQSFLEVSYRVLRHLAQPSGGG |
| | | | GSGGGGSGGGGSGGGGSGGGGSGGGG |
| | | | SGGGGSTPLGPASSLPQSFLLKCLEQVRKI |
| | | | QGDGAALQEKLCATYKLCHPEELVLLGHSL |
| | | | GIPWAPLSSCPSQALQLAGCLSQLHSGLFL |
| | | | YQGLLQALEGISPELGPTLDTLQLDVADFAT |
| | | | TIWQQMEELGMAPALQPTQGAMPAFASAF |
| | | | QRRAGGVLVASHLQSFLEVSYRVLRHLAQ |
| | | | P |
| SEQ ID No: 11 | dGCSF-Lα | 42,52 | MTPLGPASSLPQSFLLKCLEQVRKIQGDGA |
| | | | ALQEKLCATYKLCHPEELVLLGHSLGIPWA |
| | | | PLSSCPSQALQLAGCLSQLHSGLFLYQGLL |
| | | | QALEGISPELGPTLDTLQLDVADFATTIWQQ |
| | | | MEELGMAPALQPTQGAMPAFASAFQRRAG |
| | | | GVLVASHLQSFLEVSYRVLRHLAQPSGLEA |
| | | | EAAAKEAAAKEAAAKEAAAKALEAEAAAKE |
| | | | AAAKEAAAKEAAAKALEGSTPLGPASSLPQ |
| | | | SFLLKCLEQVRKIQGDGAALQEKLCATYKL |
| | | | CHPEELVLLGHSLGIPWAPLSSCPSQALQL |
| | | | AGCLSQLHSGLFLYQGLLQALEGISPELGP |
| | | | TLDTLQLDVADFATTIWQQMEELGMAPALQ |
| | | | PTQGAMPAFASAFQRRAGGVLVASHLQSF |
| | | | LEVSYRVLRHLAQP |

Figure 1:
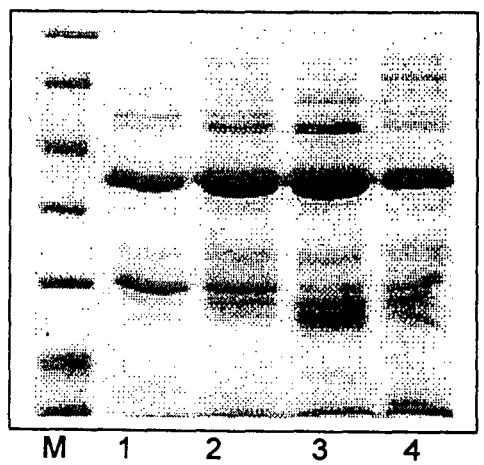
FIG. 1 shows SDS-PAGE (15%) of dimeric IFN-alpha-2a during purification on SP-Sepharose Fast Flow in reducing conditions (Coomassie staining).

Molecular mass of dimeric protein is evaluated on SDS-PAGE in reducing conditions (FIG. 1 and FIG. 2) and confirmed by mass-spectroscopy analysis. FIG. 2 also served as indication that there are no traces of —S—S— linked G-CSF dimer form. Correctness of purified dimeric protein structure and its identity is evidenced upon interaction with specific antibodies against monomeric G-CSF as has been demonstrated in Western blot analysis (FIG. 3) where efficient response has been shown in the same manner for both proteins dimeric and monomeric G-CSF. Isolation and purification of the homo-multimers of therapeutic proteins produced according to the present invention is accomplished by the procedure established for purification of respective multimer form of therapeutic protein of interest (as in Example 3, below). Purity of isolated dimeric proteins is tested using reverse phase HPLC (RP-HPLC, FIG. 4) and size exclusion chromatography HPLC (SEC-HPLC, FIG. 5). Biologic activity of the dimeric proteins obtained is tested in vitro using proliferation test on murine cell line of myeloidic leukemia G-NFS-60 (as in Example 4, below) and in vivo test on the rats detecting number of neutrophils after injection of dimeric proteins (as in Example 6, FIG. 7). The concentration changes of dimeric proteins in the serum of rats' blood are also tested after injection and compared to the control monomeric protein (Example 5, FIG. 6).

Finally purified substance of homo-multimer protein produced according to the present invention is further formulated adding pharmaceutically acceptable carrier, diluent, excipient and/or auxiliary substances and used for therapeutic purposes in indications where monomer molecule of therapeutic protein is used (e.g. antiviral indications for IFN-alpha and Neutrogena treatment indications for G-CSF).

Pharmaceutical composition of produced homo-multimer proteins according to the present invention could be formulated adding one or several components such as manitol, sorbitol, glucose, sacharose as carriers; acetate, phosphates, Tris, Hepes as pH regulating substances; mineral salts as substances for isotonic stabilization of composition; polisorbate 80 or 20, Pluronic type substances as surfactants; polyethilenglycol, polyvinylpyrrolidone, amino acids (methionine, arginine, histidine and others) as stabilization substances; EDTA, EGTA, IDA as chelating agents; kresol, benzyl alcohol, benzol derivatives as antimicrobial agents; glutathione, cysteine, acetylcysteine as SH agents; other auxiliary substances.

Embodiments of the Invention

Represented below is information on specific examples on preparation of new derivatives of recombinant proteins, including homo-multimers of GCSF, and properties thereof.

These examples are presented for illustrative purpose and are not limiting the scope of the present invention.

EXAMPLE 1

Biosynthesis and Purification of Homo-Dimer of Recombinant Human Interfenon Alpha-2a (dIFN-2a) Protein The bacterial strain producing dimeric IFN alpha-2a (dIFN-2a) *E. coli* BL21 (DE3) pET-21 IFN-L3-IFN was constructed using synthetic DNA fragment, coding the amino acid sequence of dimeric protein dIFN-alpha-2a-L3 (SEQ ID No:6, Table 2) after insertion into the expression plasmid pET-21b (Novagen). The DNA sequence of the plasmid was confirmed by direct sequencing. Bacterial strain, producing the dimeric IFN alpha-2a protein was obtained after transformation of *E. coli* BL21 (DE3) strain with the selected recombinant vector. The producer has been cultivated in 21 flasks. Medium was composed from 45,12 g M9 salts, 20 g yeast extract, 80 ml 20% glucose, 8 ml 1M MgSO$_4$, 4 ml ampicillin 100 mg/ml. Expression of target protein was induced by IPTG (isopropyl-beta-D-thiogalactopiranoside). Final concentration of IPTG was 100 mM added when optical density (OD) reached 1.2 and cultivated additionally for 2-3 h. The biomass obtained have been frozen at −20° C. and used for further protein purification process.

9,4 g of frozen *E. coli* biomass is homogenized in 50 ml of 0.1 M Tris-HCl buffer, pH 8.5 containing 1 mM EDTA (ethylenediaminetetraacetic acid). Into obtained cell suspension 0.1% Triton X-100, 1% of 100 mM PMSF(phenylmethanesulfonyl fluoride) and 100 mM of β-mercaptoethanol is added. Homogenization mixture is mixed for 1 hour at ambient temperature, further is sonicated by ultrasonic in ice and finally centrifuged at 20.000 g for 15 min. Supernatant is removed and the collected pellet of inclusion bodies (IB) is twice washed by homogenization in 200 ml of washing buffer consisting of 1 M NaCl containing 0.1% of polysorbate 80, After each homogenization cycle the suspension of IB was centrifuged at 24,500 g for 15 min. Pre-washed IB are solubilized overnight in denaturation buffer of 50 mM Tris-HCl, pH 7.0 containing 6M guanidine hydrochloride (GuHCl) and centrifuged. Supernatant is diluted 20 times with the buffer: 100 mM Tris/HCl, pH 8.0, 0.5M L-arginine/HCl, 0,1mM EDTA, 1mM L-cysteine, 0.05 mM cystin. Renaturation is running for 45 h in 22° C. with slow mixing. Incubation buffer is dialysed in sodium acetate buffer pH 5,5 and loaded onto SP-Sepharose Fast Flow column. Desorption is performed with 0-0.5 M gradient of NaCl. Fractions of eluate containing target protein are combined and go to final formulation of pharmaceutical substance.

EXAMPLE 2

Biosynthesis of Homo-Dimer of Recombinant Human G-CSF (dG-CSF) Protein

The bacterial strain producing dimeric G-CSF (dG-CSF) *E. coli* BL21 (DE3) pET-21 GCSF/L5/GCSF was constructed using synthetic DNA fragment coding the amino acid sequence of dimeric protein dGCSF-L5 (see SEQ ID No:9, Table 2) after insertion into the expression plasmid pET-21b (Novagen). The DNA sequence of the plasmid was confirmed by direct sequencing. Bacterial strain producing the dimeric G-CSF protein was obtained after transformation of *E. coli* BL21 (DE3) strain with the selected recombinant vector. The producer have been cultivated in 21 flasks or in fermenter (Sartorius AG, 5L working volume). Medium was composed from 45,12 g M9 salts, 20 g yeast extract, 80 ml 20% glucose, 8 ml 1M MgSO$_4$, 4 ml ampicillin 100mg/ml. Regulated parameters in fermenter were: temperature 37° C.; pH 6,8 (acid or base), aeration (pO$_2$ 25-30%; 1.0-1.3 l/min, O$_2$ concentration was regulated by stirring intensity). Separately the optical density of culture was registered, which is indicating the amount of biomass obtained. Expression of target protein was induced by IPTG (isopropyl-beta-D-thiogalactopiranoside). Final concentration of IPTG was 100 mM added when OD reached 1.2 and cultivated additionaly for 2-3 h. The biomass obtained have been frozen at −20° C. and used for further protein purification process.

EXAMPLE 3

Isolation and Purification of Homo-Dimer of Recombinant Human G-CSF (dG-CSF Protein) in Which Monomer Units Are Genetically Connected Via Alpha-Helical Linker Lα

2.5 g of frozen *E. coli* biomass is homogenized in 50 ml of 0.1 M Tris-HCl buffer, pH 7.0 containing 5 mM EDTA. Into obtained cell suspension 0.1% lyzozyme, 0.1% Triton X-100, 1% of 100 mM PMSF and 0.7% of β-mercaptoethanol is added. Homogenization mixture is mixed for 30 min. at ambient temperature, further is sonicated by ultrasonic in ice bath and finally centrifuged at 24,500 g for 25 min. Supernatant is removed and the collected pellet of inclusion bodies (IB) is twice washed by homogenization in 50 ml of washing buffer, containing 1 M NaCl and 0.1% of polysorbate 80 and 50 ml of water for the third washing cycle. After each homogenization cycle the suspension of IB was centrifuged at 24,500 g for 25 min. Pre-washed IB are solubilized in denaturation buffer of 50 mM Tris-HCl, pH 8.0 containing 8 M urea, 1.0 mM EDTA and optionaly 100 mM of β-mercaptoethanol. 03.5 mM, or 2.0 mM, or 1.0 mM, or 0.1 mM, or 0 mM of DTT (dithiotreithol) is used.

Solubilization of IB is done by mixing overnight at +4° C. After that the solubilizate of IB is centrifuged at 24,500 g for 25 min. and diluted with 50 mM Tris-HCl buffer, pH 8.0 containing 3 M urea and 1 mM EDTA to the final protein concentration of 0.5 mg/ml (Bradford assay). Then IB refolding is performed in the presence of GSSG in a such manner that final molar ratio in solution of DTT/GSSG is equal to 1:6 and the refolding occurred by mixing for 90 h at +4° C.

After each refolding procedure the protein solution is centrifuged at 40.000 g for 25 min. to remove formed precipitate. Clarified protein solution is loaded onto chromatography column, containing 75 ml of anion-exchanger DEAE-Sepharose Fast Flow, equilibrated with 10 mM Tris-HCl buffer, pH 7.5 containing 20 mM NaCl or 10 mM Tris-HCl buffer, pH 7.5 at a linear flow-rate of 75 cm/h. The column is washed with the initial buffer of chromatography and the target protein is eluted by NaCl gradient from 20 mM to 80 mM over 1.4 column volume (CV) and further to 450 mM over 4 CV. Fractions of eluate containing target protein are pooled (assay by RP-HPLC) for further step of chromatography purification over SP-Sepharose FF column. For this purpose, the combined pool of fractions recovered from DEAE-Sepharose FF column is adjusted with 20 mM sodium acetate buffer pH 5,4 up to conductivity of 3.2 mS/cm and loaded onto column (XK 16/40 „Pharmacia') containing 32 ml of SP-Sepharose Fast Flow equilibrated with 20 mM sodium acetate buffer pH 5.4 containing 20 mM NaCl. Protein solution is loaded into the column at a linear flow velocity of 75 cm/h. After column washing with the same buffer the target protein is eluted by increasing NaCl concentration from 20 mM to 450 mM in 20 mM sodium acetate, pH 5.4, Fractions of eluate containing target protein (assay by RP-HPLC) are combined and go to final formulation of pharmaceutical substance.

EXAMPLE 4

Determination of Biologic Activity of Homo-Dimer of Recombinant Human G-CSF (dG-CSF Protein), Using Proliferation Test of Sensitive Cell Line Biologic activity of recombinant dG-CSF protein was detected, using murine cell line of myeloidic leukemia G-NFS-60 [Weinstein Y, lhle J N, Lavu S, Reddy E P, Truncation of the c-myb gene by retroviral integration in an interleukin 3-dependent myeloid leukemia cell line. Proc. Natl. Acad. Sci. USA, 1986, vol. 83, p. 5010-5014], Active G-CSF protein initiates proliferation of this cell line after interaction with G-CSF receptor on the surface of the cell. For determination of biologic activity of dimeric G-CSF cells G-NFS-60 were cultivated in 96 well plates for 48-72 h, adding to cultivation media different amounts of (0.1-10 ng/ml) analysed GCSF protein sample. As a control the pharmaceutical samples of Neupogen™ (Filgrastim) with known biologic activity were used. Proliferation of the cells is evaluated by colorimetric method using MTS dye. The number of viable cells is dependent on the G-CSF biological activity. Data are shown in Table 3.

TABLE 3

Biologic activity of monomer G-CSF and homo-dimer of recombinant human G-CSF (dG-CSF protein) samples

| | | Biologic activity | |
|---|---|---|---|
| No. | Preparation | IU/ml | IU/mg |
| 1 | dGCSF L3 | $3.7 \cdot 10^6$ | $2.3 \cdot 10^7$ |
| 2 | dGCSF-L5 | $21.7 \cdot 10^6$ | $1.57 \cdot 10^7$ |
| 3 | dGCSF-L7 | $10.8 \cdot 10^6$ | $2.16 \cdot 10^7$ |
| 4 | dGCSF-Lα | $7.05 \cdot 10^6$ | $3.06 \cdot 10^7$ |
| 5 | Monomer G-CSF | $60.0 \cdot 10^6$ | $10.0 \cdot 10^7$ |

The results obtained indicate that the G-CSF protein structures invented and purified with the proposed methods provide the biologically active dimeric protein.

EXAMPLE 5

Pharmacokinetic Study of Homo-Dimer of Recombinant Human G-CSF (dG-CSF Protein) in Blood Serum For pharmacokinetic study of recombinant proteins in blood serum experimental animals (Wistar rats) have been divided into the groups, 4-5 rats in each. Control and analysed proteins have been injected subcutaneously. Injection doses used were from 100 to 1100 µg/kg. Neupogen™ (Filgrastim) was used as control in the same concentrations calculated to the same rat weight. Blood serum was collected 3, 6, 12 and 18 h post injection. Collected blood samples were centrifuged and serum was sterilely taken, aliquated and frozen at −80° C. Blood serum samples have been tested according to manufacture instructions using G-CSF detection DuoSet kits of R&D company using ELISA method. Results (FIG. 6) are indicating that concentration of dG-CSF in rat serum remains higher than control data during all 18 h of experiment except first three hours.

EXAMPLE 6

Pharmacodynamic Analysis of Biologic Effect of Homo-Dimmer of Recombinant Human G-CSF (dG-CSF Protein)

For pharmacokinetic analysis of recombinant proteins on the blood cells experimental animals (Wistar rats) have been divided into the groups, 4-5 rats in each. Control and analysed proteins have been injected subcutaneously. Injection doses used were from 100 to 1100 µg/kg. Neupogen™ (Filgrastim) was used as control in the same concentrations calculated to the same rat weight. Blood samples have been collected 24, 48, 72, 96 h post injection. Rat blood cells were analysed in blood analyser Hemavet 950. Biologic effect of dimeric protein was tested analysing the number of blood neutrophils before and after injection of protein samples. 20 µl of blood was taken from rat tail vein, mixed with 5 µl of 7.5% EDTA, incubated for 10 min. and analysed with Hemavet 950, Results are represented in FIG. 7, showing that effect of dimeric protein (dG-CSF) on the blood cells (the number of neutrophils) is exceeding control data.

The examples performed allow to conclude that tested homo-dimer of G-CSF (dG-CSF) proteins have biologic activity in vitro and in vivo, that is similar to the effect of control monomeric GCSF protein. Constructed homo-dimeric G-CSF proteins showed some new valuable PK/PD features, such as prolonged positive influence on neutrophil number and increased circulation time of protein in rat blood in comparison with monomeric G-CSF protein. This characteristic feature of homo-dimer of G-CSF provide possibility for its use in clinical therapy instead of monomer of G-CSF, when the time of administration of G-CSF drug preparation, e.g. Neupogen shorter than two weeks is needed, since there long-acting pegylated form of G-CSF preparation, e.g. Neulasta is not acceptable. From the other side, the effective therapeutic dose of homo-dimer of G-CSF is expected to be much more lower than of Neulasta preparation.

Proposed according the present invention new approach for increasing in vivo circulation half-life time of recombinant proteins of therapeutic values distinguished in that genetic fusion of protein monomer unit into homo-multimers do not necessary leads to decrease of biological activity—the common problem for all known therapeutic proteins with extended circulation half-life. Moreover, properly selected linker between monomer units allows each monomer specifically interact with receptors and increase the biological activity. Increased biological activity is defined herein as a prolonged plasma half-life or higher potency. This may require reduction of the frequency of administration or reduction of the quantity of protein multimer to achieve an effective dose characteristic to monomer unit of the multimer construction.

Currently marketed second-generation therapeutic proteins produced via pegylation approach exhibit lower biological activity in comparison to non-modified proteins and consequently requires higher protein amount per dose than the first generation analogues.

For example, therapeutic dose of Neulasta (PEG-G-CSF) is 6 mg instead of 0.30-0.48 mg for Neupogen (G-CSF). Therefore, proposed new approach according to the present invention for increasing of in vivo circulation time of recombinant proteins of therapeutic values will decrease protein amount per therapeutic dose.

In general, the proposed method of the genetic fusion of therapeutic protein molecule into homo-multimer, particularly homo-dimer, structure by connecting monomer units via properly selected sequence of linker moiety allows to achieve biologically active dimer with enhanced in vivo circulation time. This method distinguished from known method of multimer production in that genetical fusion assures reproducibility of quality parameters of finally purified product in comparison with the procedure of chemical conjugation. Monomer units of selected therapeutic protein are fused into homo-dimer with the aid of linker sequence with assumption that the length and structure of the linker of choice is sufficient for each monomer unit interaction with specific receptor, antibody and so on.

On the other hand the method of present invention of homo-multimers production based on recombinant DNA technologies is more technologically attractive in comparison with chemical modification and allows to produce active pharmaceutical substance of interest with consistent quality. The genetic fusion of protein monomer units into homo-multimers will avoid increase of immunogenicity and toxicity effects of the fusions, since structure of monomer units remains unaffected.

This also enable to ensure that the extension of in vivo circulation half-life is achieved without any invasion on the native structure of the monomer unit with respect to replacement/addition or deletion of amino acid residue and further modification with polymer macromolecules like PEG. The proposed method may be expanded on practically all currently known therapeutic protein with emphasis on those representatives which naturally exist in vivo as dimers.

The invention claimed is:

1. Derivatives of recombinant proteins, the derivatives comprising homo-multimers of genetically fused recombinant biologically active protein monomer units, the protein monomer units being connected via peptide linker moieties, wherein each protein monomer unit comprises an amino acid sequence of a native biologically active protein or an amino acid sequence having at least 95% identity to the sequence of the native biologically active protein, wherein each peptide linker moiety is represented by an amino acid sequence SGLEA-(EAAAK)$_m$-ALEA-(EAAAK)$_m$-ALEGS, wherein m=2-8.

2. The derivatives of recombinant proteins according to claim 1, wherein each peptide linker moiety is represented by an amino acid sequence of SEQ ID NO: 5.

3. The derivatives of recombinant proteins according to claim 1, wherein at least one peptide linker moiety is represented by an amino acid sequence of SEQ ID No: 5.

4. The derivatives of recombinant proteins according to claim 1, wherein the homo-multimers each comprise a single chain of at least two protein monomer units selected from the group consisting of cytokines, growth factors, and hormones, wherein the cytokines comprise interleukines, colony stimulating factors, or interferons.

5. The derivatives of recombinant proteins according to claim 1, wherein the protein monomer units are each recombinant human granulocyte colony-stimulating factor (rhG-CSF).

6. Homo-multimers of granulocyte colony-stimulating factor, the homo-multimers each comprising at least two genetically fused recombinant granulocyte colony-stimulating factor protein monomers connected via the peptide linker moiety defined in claim 3.

7. Homo-multimers of granulocyte colony-stimulating factor according to claim 5, wherein the homo-multimer is a dimmer which has the amino acid sequence of SEQ ID NO: 11.

8. Homo-multimers of granulocyte colony-stimulating factor according to claim 5, characterised by increased circulation time in vivo.

9. Homo-multimers of granulocyte colony-stimulating factor according to claim 5 for use in therapy.

10. A granulocyte colony-stimulating factor according to claim 5 for use in manufacture of a medicament for treating diseases.

11. A pharmaceutical composition comprising a therapeutically effective amount of homo-multimers of granulocyte colony-stimulating factor according to claim 5 in combination with a pharmaceutically acceptable carrier, diluent, excipient, auxiliary substance, or combinations thereof.

12. Dimers of the derivatives of recombinant proteins according to claim 1 produced by a method comprising:
   a) cultivating a microorganism having a nucleotide sequence encoding a target genetically fused protein in a culture medium under conditions permitting expression of the target genetically fused protein;
   b) lysing the microorganism and separating a fraction of insoluble target genetically fused proteins;
   c) solubilizing of the fraction of insoluble target genetically fused proteins;
   d) renaturing the target genetically fused proteins;
   e) chromatographically purifying the target genetically fused proteins,
   wherein:
   solubilizing the fraction of insoluble target genetically fused proteins is performed in a buffer system containing urea or guanidine hydrochloride as a chaotropic agent in the presence of a reducing agent;

renaturing comprises oxidizing renaturing of the target genetically fused protein from inclusion bodies in the presence of the reducing agent, such as reduced glutathione (GSH) or dithiothreitol, and an oxidizing agent, such as oxidized glutathione, metal ions in solution, or immobilized metal ions on a chromatography support, and chromatographically purifying comprises purifying by metal ion affinity chromatography, and further additional purification by at least one of ion-exchange or gel-filtration chromatography, or by a combination of the ion-exchange chromatography with sequential use of anion-exchange and cation-exchange chromatography.

* * * * *